US012564630B2

(12) United States Patent
David

(10) Patent No.: US 12,564,630 B2
(45) Date of Patent: Mar. 3, 2026

(54) VACCINE ADJUVANTS

(71) Applicant: VIROVAX LLC, Lawrence, KS (US)

(72) Inventor: Sunil Abraham David, Lawrence, KS (US)

(73) Assignee: VIROVAX LLC, Lawrence, KS (US)

( * ) Notice: Subject to any disclaimer, the term of this patent is extended or adjusted under 35 U.S.C. 154(b) by 663 days.

(21) Appl. No.: 17/918,249

(22) PCT Filed: May 4, 2021

(86) PCT No.: PCT/US2021/030658
§ 371 (c)(1),
(2) Date: Oct. 11, 2022

(87) PCT Pub. No.: WO2021/226088
PCT Pub. Date: Nov. 11, 2021

(65) Prior Publication Data

US 2023/0148332 A1 May 11, 2023

Related U.S. Application Data

(60) Provisional application No. 63/020,418, filed on May 5, 2020.

(51) Int. Cl.

| | |
|---|---|
| ***A61K 39/39*** | (2006.01) |
| ***A61K 39/00*** | (2006.01) |
| ***A61K 45/06*** | (2006.01) |
| ***C07D 471/04*** | (2006.01) |

(52) U.S. Cl.
CPC .............. *A61K 39/39* (2013.01); *A61K 45/06* (2013.01); *C07D 471/04* (2013.01); *A61K 2039/55511* (2013.01)

(58) Field of Classification Search
CPC .......... A61K 2039/55511; A61K 39/39; A61K 45/06; C07D 471/04
USPC ...................................................... 514/235.2
See application file for complete search history.

(56) References Cited

U.S. PATENT DOCUMENTS

| | | | | |
|---|---|---|---|---|
| 6,083,505 A | 7/2000 | Miller et al. | | |
| 9,441,005 B2 * | 9/2016 | David et al. | ......... | C07D 471/04 424/193.1 |
| 9,441,995 B2 * | 9/2016 | Goddard et al. | ..... | C07D 471/04 424/193.1 |
| 10,618,896 B2 * | 4/2020 | Chipman et al. | .... | C07D 471/04 |
| 2018/0134701 A1 | 5/2018 | David et al. | | |
| 2019/0151462 A1 | 5/2019 | Coffman et al. | | |

OTHER PUBLICATIONS

United States Patent and Trademark Office; International Search Report and Written Opinion issued in Int'l App. No. PCT/US2021/030658 dated Sep. 2, 2021; 8 pages.

(Continued)

*Primary Examiner* — Jeffrey S Lundgren
*Assistant Examiner* — Heather Dahlin
(74) *Attorney, Agent, or Firm* — MASCHOFF BRENNAN

(57) ABSTRACT

A compound comprising a structure of Compound 1, or prodrug thereof, salt thereof, or tautomer, polymorph, solvate, or combination thereof, can be used as an adjuvant in vaccines. The Compound 1 can be used in: methods of performing a vaccination; methods of agonizing a TLR 7 and/or TLR 8; and/or methods of activating an immune system.

12 Claims, 6 Drawing Sheets

IMDQ-*m*-Amine

IMDQ-*m*-Amine-Gallamide 3,4,5-trihydroxybenzoic acid 1-(3-(aminomethyl)benzyl)-2-butyl-1*H*-imidazo[4,5-c]quinolin-4-amine

*N*-(3-((4-amino-2-butyl-1*H*-imidazo[4,5-c]quinolin-1-yl)methyl)benzyl)-3,4,5-trihydroxybenzamide

(56) References Cited

OTHER PUBLICATIONS

Pubchem; "SID 393258796"; webpage; Dec. 6, 2019; located at: https://pubchem.ncbi.nlm.nih.gov/substance/393258796.
Pubchem; "SID 89987971"; webpage; May 5, 2011; webpage: located at: https://pubchem.ncbi.nlm.nih.gov/substance/89987971.
Wang et al.; "Potent and Prolonged innate immune activation by enzyme-sensitive imidazoquinoline TLR7/8 agonist prodrug vesicles"; Journal of American Chemical Society; vol. 142, Issue 28; Jul. 15, 2020; https://www.ncbi.nlm.nih.gov/pmc/articles/PMC7116109.

* cited by examiner

IMDQ-*m*-Amine

IMDQ-*m*-Amine-Gallamide 1-(3-(aminomethyl)benzyl)-2-butyl-1*H*-imidazo[4,5-c]quinolin-4-amine 3,4,5-trihydroxybenzoic acid

*N*-(3-((4-amino-2-butyl-1*H*-imidazo[4,5-c]quinolin-1-yl)methyl)benzyl)-3,4,5-trihydroxybenzamide 48 h 24 h Rabbit Immunization: Prime + Boost (Two-dose) Regimen VV-16. Imm-1. nAb Titers: Alhydrogel and Alhydroxiquim-II Cohorts Means of Duplicates SARS-CoV-2 Isolate USA-WA1/2020 (BEI-R # NR-52281)

Cohort-1 (Alhydrogel)
1.R1402.Preimm
1.R1403.Preimm
1.R1404.Preimm
1.R1405.Preimm
1.R1402.Imm1
1.R1403.Imm1
1.R1404.Imm1
1.R1405.Imm1

Cohort-2 (Alhydroxiquim-
2.R1406.Preimm
2.R1407.Preimm
2.R1408.Preimm
2.R1409.Preimm
2.R1406.Imm1
2.R1407.Imm1
2.R1408.Imm1
2.R1409.Imm1

Serum Dilution Factor

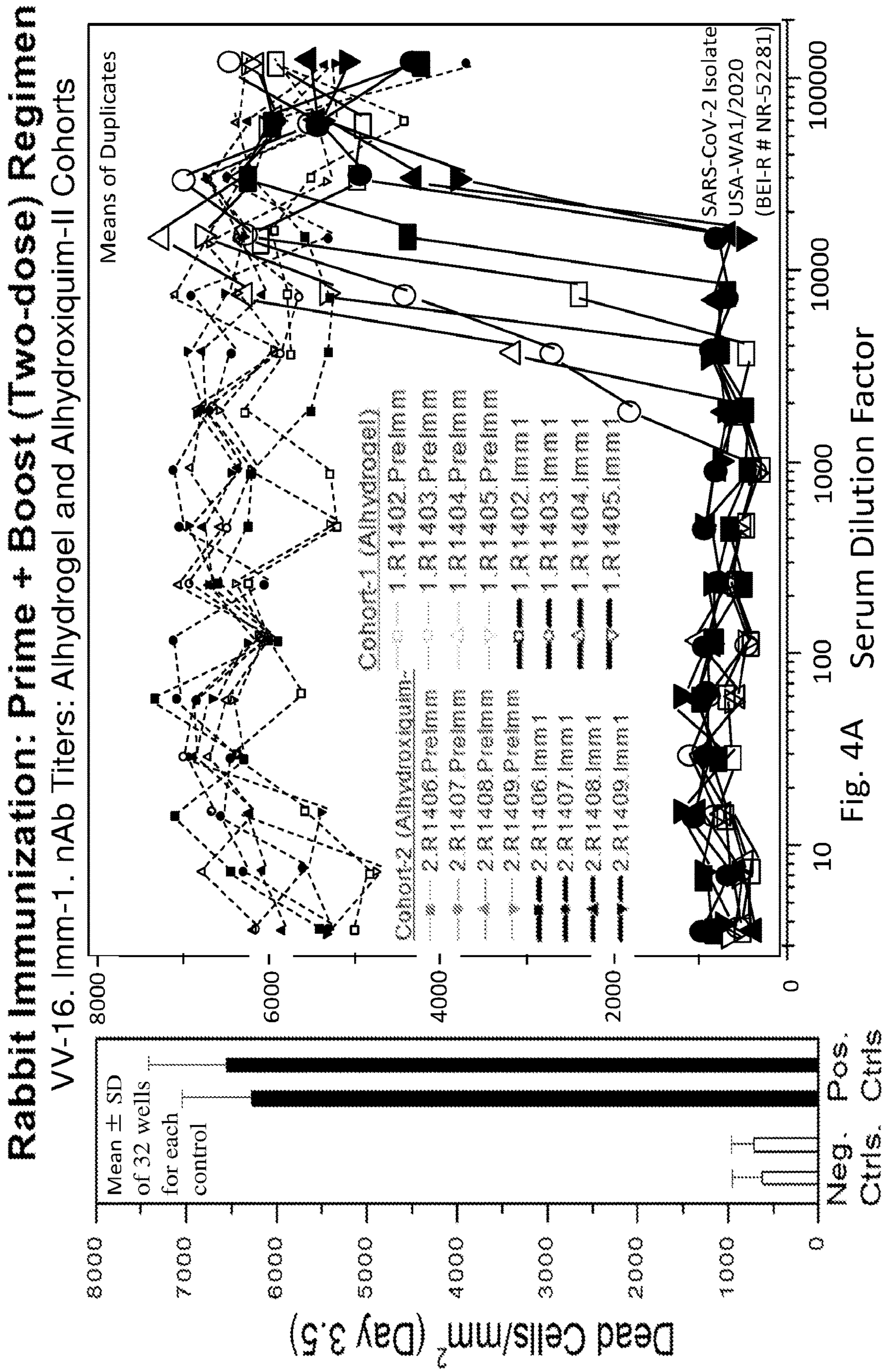

Fig. 4A

Dead Cells/mm$^2$ (Day 3.5)

Mean ± SD of 32 wells for each control

Pos. Ctrls

Neg. Ctrls

VACCINE ADJUVANTS

CROSS-REFERENCE TO RELATED APPLICATIONS

This patent application claims priority to U.S. Provisional Application No. 63/020,418 filed May 5, 2020, which provisional is incorporated herein by specific reference in its entirety.

BACKGROUND

Field

The present disclosure relates to compounds and/or materials for use as adjuvants for vaccines. For example, the compound described herein can be used as an adjuvant in a vaccine for influenza or SARS-CoV-2 or other viruses.

Description of Related Art

Vaccines have resulted in the eradication or dramatic reduction in number of diseases such as smallpox, polio, and tetanus. Nevertheless, there is still a pressing need for new vaccines for diseases for which sufficiently effective vaccines do not exist, but also to replace reactogenic vaccines with safer alternatives.[1]

In order to achieve a high level of efficacy and safety, many newer vaccines with more defined composition that is often linked to lower immunogenicity rely on potent immunostimulants (vaccine adjuvants).[2] The Food and Drug Administration (FDA) considers an adjuvant to a substance added to vaccines to enhance the immune response in vaccinated individuals. Adjuvants also serve to reduce the amount of antigen needed for the induction of a robust immune response ('dose-sparing effect') or the number of immunizations needed for protective immunity. The ability of adjuvants to broaden antibody responses could be crucial for the success of vaccines against many pathogens that display substantial antigenic drift and/or strain variations including influenza viruses, human immunodeficiency virus (HIV), human papilloma virus (HPV), and the malaria parasite.[3] Adjuvants also help improve the efficacy of vaccines in newborns, the elderly or immunocompromised persons, or can be used as antigen delivery systems for the uptake of antigens.[4]

Vaccine adjuvant research has expanded rapidly in the past decade and has directly benefited from our evolving understanding of immunology, beginning with the recognition of the cellular elements involved in innate immunity, and growing to encompass the elucidation of the mechanisms of recruitment of adaptive immune effector pathways. Knowledge of the molecular mechanism of innate immune activation has also afforded a large number of potential new targets for immune stimulators.[5] Numerous receptors and signaling pathways in the innate immune system have been defined. Unlike adaptive immunity, the initial innate immune responses rely on a limited number of germline-encoded pattern recognition receptors (PRRs), which recognize specific molecular patterns present in molecules that are broadly shared by pathogens but are sufficiently different so as to be distinguishable from host molecules, and are collectively referred to as pathogen-associated molecular patterns (PAMPs).[6] PRRs are classified according to their structural homology: Toll-like receptors (TLRs), RIG-I-like receptors (RLRs),[7] NOD-like receptors (NLRs),20 and C-type lectin receptors (CLRs).[8]

The TLR family is one of the well-studied targets in terms of ligands, downstream signaling pathways, and functional relevance. There are 10 TLRs in the human genome; these are transmembrane proteins with an extracellular domain having leucine-rich repeats (LRR) and a cytosolic domain called the Toll/IL-1 receptor (TIR) domain. The ligands for these receptors are highly conserved microbial molecules such as lipopolysaccharides (LPS) (recognized by TLR4), lipopeptides (TLR2 in combination with TLR1 or TLR6), flagellin (TLR5), single stranded RNA (TLR7 and TLR8), double stranded RNA (TLR3), CpG motif-containing DNA (recognized by TLR9), and profilin present on uropathogenic bacteria (TLR11). TLR1, -2, -4, -5, and -6 recognize extracellular stimuli, while TLR3, -7, -8 and -9 function within the endolysosomal compartment.[9] The activation of TLRs by their cognate ligands leads to production of inflammatory cytokines, and up-regulation of major histocompatibility complex (MHC) molecules and co-stimulatory signals in antigen-presenting cells as well as activating natural killer (NK) cells (innate immune response), in addition to priming and amplifying T-, and B-cell effector functions (adaptive immune responses).[10] TLR stimuli serve to link innate and adaptive immunity and therefore there is considerable interest in utilizing TLR agonists as vaccine adjuvants.[11]

A potential drawback in using small-molecule TLR agonists as vaccine adjuvants is their propensity to diffuse out of the vaccination site into systemic circulation, thereby not only limiting their adjuvantic properties but perhaps also enhancing the risk of systemic reactogenicity. The administration of Resiquimod, for instance, was poorly tolerated in human preclinical trials, with systemic side effects including fever, headache, malaise, and myalgia,[12] likely due to systemic immune activation. Limiting systemic exposure has recently been addressed by adsorbing small molecules incorporating phosphonate groups on "alum" [$Al(OH)_3$].[13] Aluminum hydroxide (commonly referred to as "Alum") is an FDA-approved vaccine adjuvant in common use.

Numerous studies in our laboratories[14] have shown that physiological concentrations of phosphate present in blood and other extracellular or interstitial fluids can displace phosphate- and phosphonate-containing molecules. In order to circumvent the problem of dissociation of the "alum"-bound small molecules (and subsequent systemic exposure and associated reactogenicity), we have explored a variety of strategies to minimize systemic exposure of the TLR agonist(s) while maximizing delivery to draining lymph nodes.[15]

SUMMARY

In some embodiments, a compound comprising a structure of Compound 1, or prodrug thereof, salt thereof, or tautomer, polymorph, solvate, or combination thereof, Compound 1

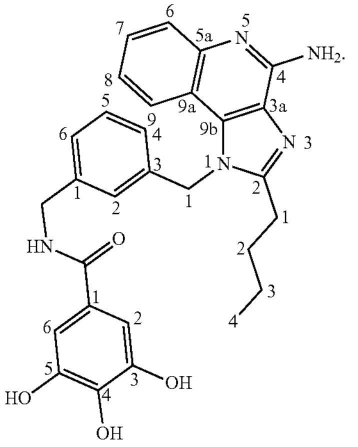

In some embodiments, a composition can include the Compound 1 and a pharmaceutical carrier having the compound. In some aspects, the composition can include an immunological vaccine agent (e.g., having an antigen and immunogenicity) in the pharmaceutical carrier with the compound. The composition can be administered to a subject in order to provide antigen-specific immunity to the antigen.

In some embodiments, a complex can include Compound 1 and a particle having the compound associated therewith. In some aspects, the particle is an aluminum hydroxide particle. In some aspects, the association is chemisorption.

In some embodiments, a method of performing a vaccination can include administering the composition having Compound 1 to a subject to provide the compound in an amount sufficient to function as an adjuvant with regard to the immunological vaccine agent.

In some embodiments, a method of agonizing a TLR 7 and/or TLR 8 can include providing the Compound 1 to TLR 7 and/or TLR 8 in an amount sufficient to agonize the TLR 7 and/or TLR 8.

In some embodiments, a method of activating an immune system can include administering the composition having Compound 1 to a subject along to provide the compound in an amount sufficient to function as an adjuvant with regard to an immunological agent having an antigen and immunogenicity.

In some embodiments, a method of synthesizing Compound 1 can include reacting 1-(3-(aminomethyl)benzyl)-2-butyl-1H-imidazo[4,5-c]quinolin-4-amine with 3,4,5-trihydroxybenzoic acid (gallic acid) to form Compound 1.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

FIG. 4A shows the dead cells/mm$^2$ for the serum dilution factors of Alhydrogel and Alhydroxiquim-II.

Figure 1:
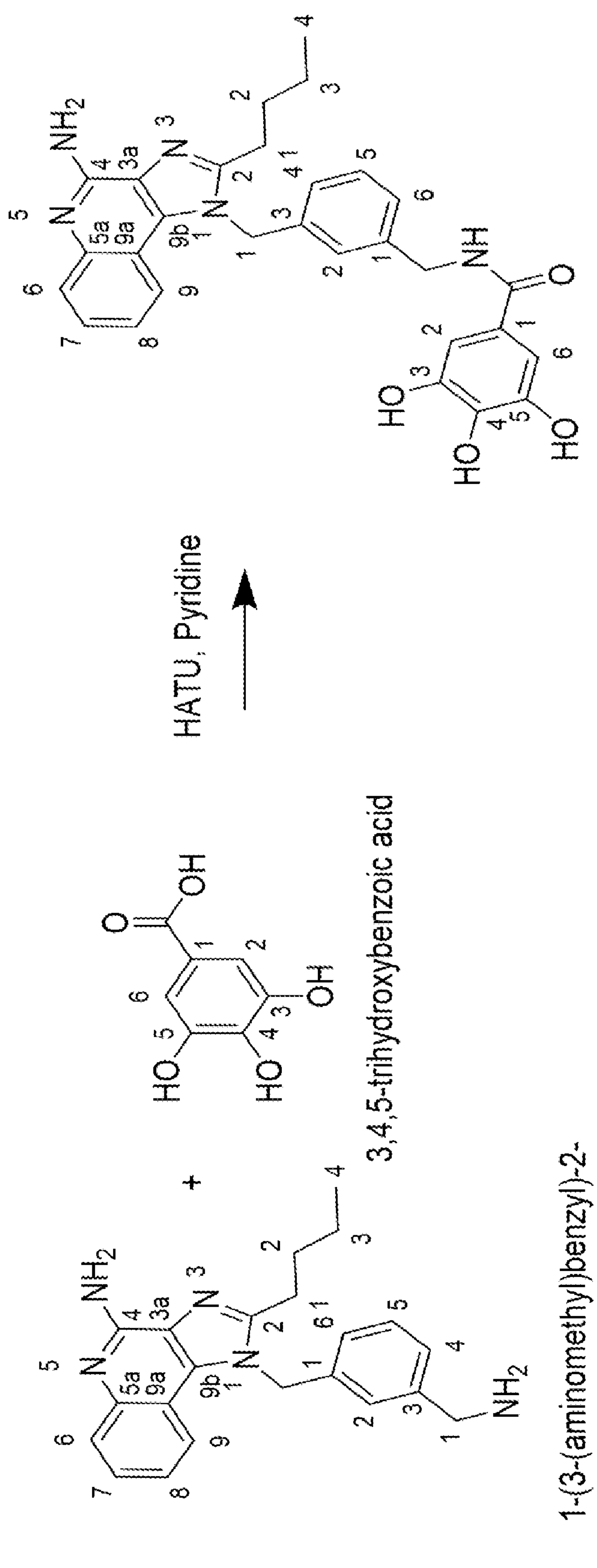
FIG. 1 shows the syntheses of N-(3-((4-amino-2-butyl-1H-imidazo[4,5-c]quinolin-1-yl)methyl)benzyl)-3,4,5-trihydroxybenzamide.

The elements and components in the figures can be arranged in accordance with at least one of the embodiments described herein, and which arrangement may be modified in accordance with the disclosure provided herein by one of ordinary skill in the art.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present technology includes an adjuvant that can be used for inducing immunity to an antigen in a subject. The adjuvant is Compound 1 as shown below, which can be used in the compound form, a chemisorbed particle form, prodrug form, or combinations thereof. The chemisorbed form includes the compound or prodrug associated with a particle, such as through chemisorption or other adsorption. The prodrug for can include any prodrug moiety, such as a phosphate, which can be coupled with the amine or hydroxyl of the Compound 1. The antigen can be any type of antigen that a subject can have immunity against, such as protein, peptide, or nucleic acid (DNA, RNA, mRNA, etc.). An immunogenic composition to induce immunity to a specific antigen can include the antigen (e.g., B-cell mediated, T-cell mediated). In some aspects, the antigen can be a purified protein or portion thereof (e.g., antigen portion), or combinations of proteins. In some aspects, the antigen can be a purified nucleic acid, such as from a pathogen. The antigen can be isolated from a natural source (e.g., from pollen or venom) or produced in a laboratory setting (e.g., from bacteria or mammalian cells configured to produce the antigen). In some aspects, the antigen can be from pollen, venom (e.g., snake, spider, etc.), bacterial, virus, fungus, or the like. The antigen can be a protein, peptide, or nucleic acid in native form or chemically modified (e.g., modified with formaldehyde, glutaraldehyde, and beta-propiolactone, etc.). The antigen can include an attenuated pathogen, such as virus, bacteria, or fungus, which includes all or part of the attenuated pathogen. The antigen can include an inactivated (e.g., killed or dead) pathogen, such as virus, bacteria, or fungus, which includes all or part of the attenuated pathogen. In some aspects, the antigen can be a protein or polypeptide. In some aspects, the antigen can be a polynucleotide (e.g., nucleic acid, such as DNA, RNA, etc.)

In some embodiments, the present technology includes novel Toll-like receptor 7 and Toll-like receptor 8 active compounds (e.g., agonists) that include functional groups. The functional groups allow the chemisorption of such Toll-like receptor 7 and Toll-like receptor 8 active compounds to the surface of aluminum hydroxide particles. Preparations having complexes of the compounds associated with the aluminum hydroxide particles allow for the targeted delivery of the Toll-like receptor 7 and Toll-like receptor 8 active compounds to draining lymph nodes with negligible systemic exposure, which results in minimal systemic reactogenicity.

In some embodiments, the Toll-like receptor 7 and Toll-like receptor 8 active compounds include a structure of one of Compound 1, or prodrug thereof, salt thereof, tautomer, polymorph, solvate, or combination thereof, Compound 1

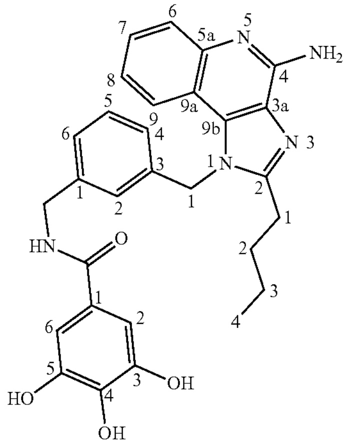

(N-(3-((4-amino-2-butyl-1H-imidazo[4,5-c] quinolin-1-yl) methyl)benzyl)-3,4,5-trihydroxybenzamide).

The Compound 1 can be provided for use as a vaccine adjuvant in a vaccine composition for immunizing (e.g., vaccinating) a subject prior to being infected with a virus. The compound acts as a vaccine adjuvant for an immunological vaccine agent in the vaccine. The compound can also be adsorbed onto a particle, such as aluminum hydroxide, to form an adjuvant complex. The vaccine adjuvant and adjuvant complex can be used for activating or agonizing TLR receptors, such as TLR7 and/or TLR8 (e.g., TLR7/8). When TLR7 and/or TLR8 are agonized or otherwise activated in a subject along with exposure to an immunological vaccine agent, the immune system can facilitate immunogenicity for the vaccine agent for immunization.

In some embodiments, the Compound 1 can be synthesized by reacting 1-(3-(aminomethyl)benzyl)-2-butyl-1H-imidazo[4,5-c]quinolin-4-amine (e.g., a compound with dual TLR7- and TLR8-agonistic properties) with 3,4,5-trihydroxybenzoic acid (gallic acid). The syntheses of N-(3-((4-amino-2-butyl-1H-imidazo[4,5-c] quinolin-1-yl)methyl) benzyl)-3,4,5-trihydroxybenzamide can be accomplished as shown in FIG. 1, which is described below. The reaction produces a conjugate in the form of Compound 1, which is capable of binding stably and saturably to $Al(OH)_3$. The adsorption of the trihydroxybenzamide moiety to the surface hydroxyl groups on aluminum hydroxide nanoparticles occurs via ligand exchange, and can be characterized as 'chemisorption'. When injected into muscle or subdermal tissue, the nanoparticles traffic to draining lymph nodes, wherein the small molecule dissociates, leading to focused immune activation within the lymph node. This results in excellent adjuvantic properties with undetectably low systemic exposure and attendant reactogenicity.

Figure 2:
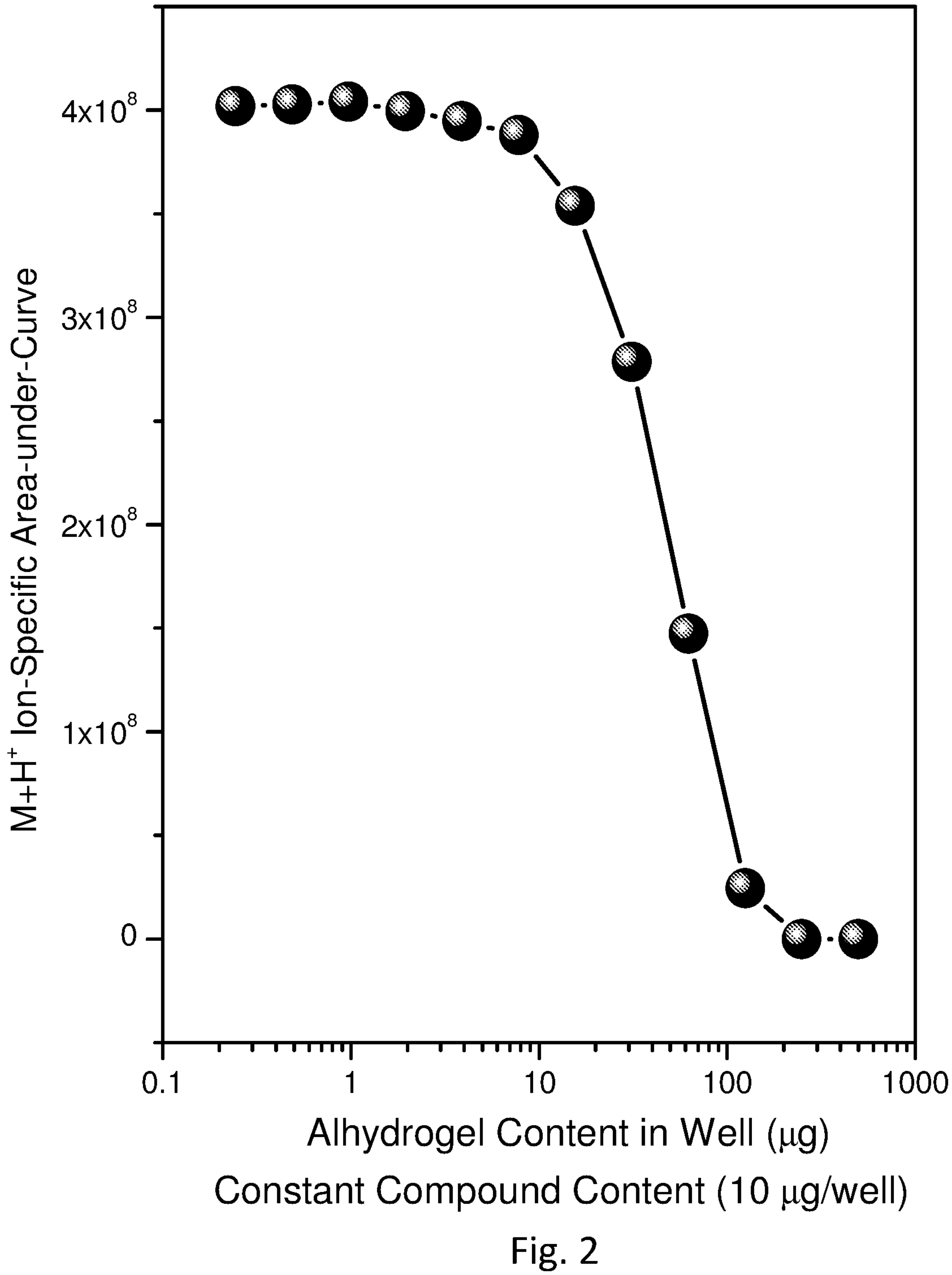
FIG. 2 shows the chemisorption of N-(3-((4-amino-2-butyl-1H-imidazo[4,5-c]quinolin-1-yl)methyl)benzyl)-3,4,5-trihydroxybenzamide to aluminum hydroxide ("Alum").

The chemisorption of N-(3-((4-amino-2-butyl-1H-imidazo[4,5-c] quinolin-1-yl)methyl)benzyl)-3,4,5-trihydroxybenzamide to aluminum hydroxide ("Alum") is shown in FIG. 2. FIG. 2 shows the chemisorption of N-(3-((4-amino-2-butyl-1H-imidazo[4,5-c]quinolin-1-yl)methyl)benzyl)-3,4,5-trihydroxybenzamide to "Alum" is saturable. Chemisorption was quantified by liquid chromatography-mass spectrometry. When appropriate ratios of the adjuvant and aluminum hydroxide are used, all of the adjuvant is bound to alum. This ensures delivery of the adjuvant to the draining lymph nodes, and minimizes systemic exposure. It is important not to exceed the ratio to avoid the presence of excess small molecule adjuvant. The ratio of small molecule adjuvant to aluminum hydroxide gel (Alhydrogel) that has been determined to provide complete binding (and consequent undetectable concentrations of free small molecule) is 10 mg of the small-molecule, N-(3-((4-amino-2-butyl-1H-imidazo[4,5-c]quinolin-1-yl)methyl)benzyl)-3,4,5-trihydroxybenzamide, to 10 mL of standard Alhydrogel (Brenntag, Denmark, 10 mg of aluminum content/mL). The ratio can range from 1:10 (mg Compound 1:mL aluminum hydroxide gel) to 10:1, or from 1:8 to 8:1, or 1:5 to 5:1; or 1:2 to 2:1, or about 1:1.

Figure 3:
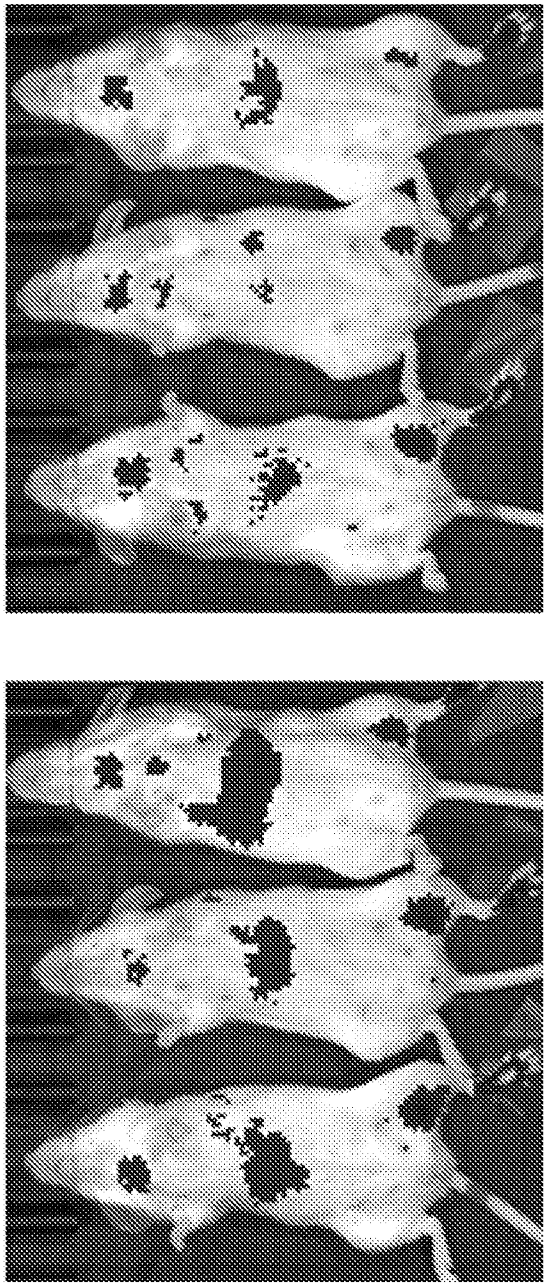
FIG. 3 shows data for trafficking to draining lymph nodes of "Alum" chemisorbed with N-(3-((4-amino-2-butyl-1H-imidazo[4,5-c] quinolin-1-yl)methyl)benzyl)-3,4,5-trihydroxybenzamide (Alhydroxiquim-II).

The trafficking to draining lymph nodes of "Alum" chemisorbed with N-(3-((4-amino-2-butyl-1H-imidazo[4,5-c] quinolin-1-yl)methyl)benzyl)-3,4,5-trihydroxybenzamide (e.g., adjuvant complex) is shown in FIG. 3. Ten micrograms of material was injected into the footpads of Interferon-beta-Luciferase reporter mice. Interferon-beta-specific luminescence was monitored intravitally. This supports the adjuvant complex can be used for an adjuvant for vaccines for preferential delivery to the lymph nodes.

In some embodiments, the Compound 1 and formulations and complexes described herein can be used as an adjuvant in pharmaceutical compositions. The pharmaceutical compositions can be immunization compositions that are used for vaccination of a subject to inhibit a viral infection. For example, the immunization compositions can include immunological vaccine agents, such as those with an antigen and immunogenicity. The vaccine agent can include a part of a virus for use in a vaccine. The Compound 1 and adjuvant complex thereof can be formulated for administration by any suitable route as described herein to a subject prior to having a viral infection in order to vaccinate the subject. The type of virus can determine the immunological vaccine agents useful or vaccination.

In some embodiments, the Compound 1 be used for activating or agonizing the TRL7 and/or TLR8 receptors. This can include activating or agonizing with the Compound 1 with or without being associated with the particle in the adjuvant complex. The Compound 1 can be used for inhibition in vitro and in vivo. Also, the adjuvant complex can be used for activating or agonizing in vivo, such as during a vaccination. Thus, activating or agonizing the TRL7 and/or TLR8 receptors can facilitate immunogenicity to the immunological vaccine agent.

In a related aspect, a vaccine pharmaceutical composition is provided, the vaccine pharmaceutical composition including an effective amount of the compound of any embodiments of compounds (or pharmaceutically acceptable salt thereof) for prophylactics purposes prior to being infected with a virus (e.g., influenza, SARS-CoV-2, etc.).

In some embodiments, the vaccine adjuvant or adjuvant complex can be used in an effective amount. The term "effective amount" refers to the amount of a compound or composition required to produce a desired effect. One example of an effective amount includes amounts or dosages that yield acceptable toxicity and bioavailability levels for therapeutic (pharmaceutical) use including, but not limited to, being used in a vaccine to improve function of the immunogenicity to the immunological agent of the vaccine. As used herein, a "subject" or "patient" is a mammal, such as a cat, dog, rodent, horse, bat, or primate. Typically the subject is a human, and, preferably, a human suffering from or suspected of suffering from an addiction. The term "subject" and "patient" can be used interchangeably.

Thus, the instant present technology provides pharmaceutical compositions and medicaments comprising the Compound 1 or adjuvant complex. The compositions may be used in the methods and treatments described herein. Such compositions and medicaments include a therapeutically effective amount of any compound or complex as described herein. The pharmaceutical composition may be packaged in unit dosage form. The unit dosage form is effective in being an adjuvant in a vaccine when administered to a subject in need thereof, or it can be within a vaccine composition with the vaccine agent.

The pharmaceutical compositions and medicaments may be prepared by mixing Compound 1 or the adjuvant complex, with pharmaceutically acceptable carriers, excipients, binders, diluents or the like to prevent or inhibit viral infection, and thereby can be used in vaccines for vaccinations. The compound, complexes, and compositions described herein may be used to prepare formulations and medicaments that prevent a variety of viral infections, such as the viruses described herein. Such compositions can be in the form of, for example, granules, powders, tablets, capsules, syrup, suppositories, injections, emulsions, elixirs, suspensions or solutions. The instant compositions can be formulated for various routes of administration, for example, by oral, parenteral, topical, rectal, nasal, vaginal administration, or via implanted reservoir. Parenteral or systemic administration includes, but is not limited to, subcutaneous, intravenous, intraperitoneal, and intramuscular, injections. The following dosage forms are given by way of example and should not be construed as limiting the instant present technology.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference.

The pharmaceutical compositions provided herein can be provided in a unit-dosage form or multiple-dosage form. A unit-dosage form, as used herein, refers to a physically discrete unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an ampoule, syringe, and individually packaged tablet and capsule. For example, a 100 mg unit dose contains about 100 mg of an active ingredient in a packaged tablet or capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein can be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

When the compound provided herein contains an acidic or basic moiety, it may also be provided as a pharmaceutically acceptable salt. See, Berge et al., *J. Pharm. Sci.* 1977, 66, 1-19; and *Handbook of Pharmaceutical Salts, Properties, and Use*; Stahl and Wermuth, Ed.; Wiley-VCH and VHCA: Zurich, Switzerland, 2002. Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-aminosalicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

The compound provided herein may also be provided as a prodrug, which is a functional derivative of the compound. For example, Compound 1 is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. For example, a phosphate prodrug can be coupled via the amine or at a different location, such as a hydroxyl. See, Harper, *Progress in Drug Research* 1962, 4, 221-294; Morozowich et al. in *Design of Biopharmaceutical Properties through Prodrugs and Analogs*; Roche Ed., APHA Acad. Pharm. Sci.: 1977.

Specific dosages may be adjusted depending on the age, body weight, general health conditions, sex, and diet of the subject, dose intervals, administration routes, excretion rate, and others. Any of the above dosage forms containing effective amounts are well within the bounds of routine experimentation and therefore, well within the scope of the instant present technology.

Those skilled in the art are readily able to determine an effective amount, such as by simply administering a compound of the present technology to a patient in increasing amounts of the adjuvant until the identification of a vaccine composition with the proper amount of adjuvant. The compounds and/or complexes of the present technology can be administered to a patient at dosage levels in the range of about 50 to about 500 micrograms per vaccination. For example, 50-500 micrograms of Alhydroxiquim-II. The specific dosage used, however, can vary or may be adjusted as considered appropriate by those of ordinary skill in the art. For example, the dosage can depend on a number of factors including the requirements of the patient, the severity of the condition being treated and the pharmacological activity of the compound being used. The determination of optimum dosages for a particular patient is well known to those skilled in the art.

Various assays and model systems can be readily employed to determine the therapeutic effectiveness of the treatment according to the present technology.

The administration may include oral administration, parenteral administration, or nasal administration. In any of these embodiments, the administration may include subcutaneous injections, intravenous injections, intraperitoneal injections, or intramuscular injections. In any of these embodiments, the administration may include oral administration.

In some embodiments, a compound of the present technology is administered to a patient in an amount or dosage suitable for vaccination. Generally, a unit dosage comprising a compound of the present technology will vary depending on patient considerations. Such considerations include, for example, age, protocol, condition, sex, extent of disease, contraindications, concomitant therapies and the like. An exemplary unit dosage based on these considerations can also be adjusted or modified by a physician skilled in the art. For example, the dosage per vaccination can be 50-500 microgram of Alhydroxiquim-II.

In some embodiments, a pharmaceutical composition can include a compound and a pharmaceutically acceptable carrier. In one aspect, the composition is configured for oral administration, parenteral administration, intravenous administration, topical administration, or subcutaneous administration. In one aspect, the Compound 1 is present in an amount sufficient for agonizing a Toll-Like Receptor (TLR), such as TLR 7 and/or TLR8. In one aspect, the composition is a vaccine and includes a vaccine agent. The vaccine agent is the entity to which the vaccine provides for immunogenicity thereto, such as by having an antigen.

In some embodiments, the compound is an adjuvant for the immunological vaccine agent. In some aspects, the immunological vaccine agent includes at least part of a virus that includes the antigen. For example, the virus is selected from the group consisting of smallpox, polio, tetanus, influenza viruses, human immunodeficiency virus (HIV), human papilloma virus (HPV), SARS-CoV-2, or other viruses described herein, and combinations thereof.

In some embodiments, the compound is formed into a complex. As such, the complex can include Compound 1 and a particle having the compound associated therewith. For example, the particle is an aluminum hydroxide particle. In some aspects, the association of Compound 1 to the particle is chemisorption.

In some embodiments, a method of agonizing a TLR 7 and/or TLR8 can include providing a compound of one of the embodiments to a TLR 7 and/or TLR8 in an amount sufficient to agonize the TLR 7 and/or TLR8. The TLR 7 and/or TLR8 can be in vitro or in vivo. The method can include agonizing the TLR7 and/or TLR8 so as to cause an adaptive immune response to an immunological agent having an antigen and immunogenicity.

In some embodiments, a method of improving vaccination can include administering a vaccine agent (e.g., having an antigen) to a subject along with a compound or complex of one of the embodiments in an amount sufficient to function as an adjuvant with regard to the vaccine agent. The improved vaccination method can include agonizing a Toll-Like Receptor 8 (TLR8) in the subject. In one aspect, the method can include agonizing the TLR8 so as to increase production of inflammatory cytokines. In one aspect, the method can include agonizing the TLR8 so as to up-regulate major histocompatibility complex (MHC) molecules and co-stimulatory signals in antigen-presenting cells. In one aspect, the method can include agonizing the TLR8 so as to activate natural killer (NK) cells. In one aspect, the method can include agonizing the TLR8 so as to cause an adaptive immune response to the vaccine agent. In one aspect, the method can include agonizing the TLR8 so as to induce production of T helper 1-polarizing cytokines. The vaccine agent can be an agent that activates the immune system so that the immune system becomes immune to the vaccine agent or at least attempts to be immune to the vaccine agent. Often, the vaccine agent includes at least a portion of a virus or at least a portion of a viral protein or viral peptide or nucleic acid thereof.

In some embodiments, method of performing a vaccination can include: providing the compound, complex, or composition of one of the embodiments described herein; and administering the composition to a subject to provide the compound in an amount sufficient to function as an adjuvant with regard to the immunological vaccine agent. In some aspects, the vaccination is for a virus selected from the group consisting of smallpox, polio, tetanus, influenza viruses, human immunodeficiency virus (HIV), human papilloma virus (HPV), SARS-CoV-2, and combinations thereof.

In some embodiments, a method of activating an immune system can include administering an immunological agent to a subject along with an adjuvant compound of one of the embodiments in an amount sufficient to function as an adjuvant with regard to the immunological agent. In some aspects, the method includes administering the composition to a subject along to provide the compound in an amount sufficient to function as an adjuvant with regard to an immunological agent having an antigen and immunogenicity. In some aspects, the method includes agonizing TLR7 and/or TLR8 in the subject so as to cause an adaptive immune response to the immunological agent.

In some aspects, the immunological agent is a virus. In some aspects, the method can include performing a vaccination for a virus, wherein the virus is selected from the group consisting of smallpox, polio, tetanus, influenza viruses, human immunodeficiency virus (HIV), human papilloma virus (HPV), SARS-CoV-2, and combinations thereof. the immunological agent is an immunological vaccine agent.

In some embodiments, the methods can include performing a vaccination for a virus with the immunological vaccine agent, wherein the virus is selected from the group consisting of smallpox, polio, tetanus, influenza viruses, human immunodeficiency virus (HIV), human papilloma virus (HPV), SARS-CoV-2, and combinations thereof.

In some embodiments, a method of synthesizing Compound 1 can include reacting 1-(3-(aminomethyl)benzyl)-2-butyl-1H-imidazo[4,5-c]quinolin-4-amine with 3,4,5-trihydroxybenzoic acid (gallic acid) to form Compound 1. See FIG. 1.

In some embodiments, Compound 1 is a TLR7 agonist that can function in protocols for immune activation, such as IFN-$\alpha/\beta/\gamma$ and cytokine induction. The Compound 1 can be a small-molecule agonist of TLR7 and be immunostimulatory by being potent inducers of Type I IFN and evoke dominant proinflammatory cytokine responses, suggesting that they may be effective, yet safe vaccine adjuvants. Compound 1 can be a Toll-like receptor (TLR)-8 agonist that strongly induces the production of T helper 1-polarizing cytokines, and may therefore serve as promising candidate vaccine adjuvants, especially for the very young and the elderly.

The immunizing composition can include the Compound 1 and a immunological vaccine agent that has an antigen and immunogenicity. The compound is an adjuvant for the immunological vaccine agent, which can improve the immune response. In some aspects, the antigen is from a natural source, such as an allergen (e.g., pollen) a toxin (e.g., venom, poison, etc.), a virus (e.g., part of the virus that has the antigen), a bacterium (e.g., part of bacterium that has the antigen), or a fungus (e.g., part of fungus that has the antigen), or other antigen-containing substances that are natural. In some instances, the antigen can be on a synthetic compound, such as a synthetic poison. In some aspects, the antigen is generated in a laboratory setting (e.g., not naturally produced in natural environment), which can include modified bacteria or mammalian cells that are configured (e.g., genetic modification, transfected, etc.) to produce the antigen.

In some aspects, the antigen is chemically modified. For example, the antigen can be chemically modified with formaldehyde, glutaraldehyde, beta-propiolactone, or combinations thereof.

In some embodiments, the antigen includes an attenuated pathogen. An attenuated pathogen is the pathogen that has reduced virulence or infectivity. For example, an attenuated vaccine is a vaccine created by reducing the virulence of a pathogen, but still keeping it viable. Attenuation takes an infectious agent and alters it so that it becomes harmless or less virulent.

In some embodiments, the antigen includes an inactivated pathogen. When inactivated, the pathogen is dead. The inactivated pathogen can be provided as whole pathogen in a dead or inactivated state (e.g., no longer virulent or capable of infection), or portion of inactivated pathogen.

In some embodiments, the antigen includes a polypeptide, protein, or portion thereof. This can include whole proteins or portions thereof, as well as polypeptides (e.g., having peptides). For example, a portion of a toxin can be used that is not toxic, in order to provide an antigen to induce immunogenicity to the toxin. Whole proteins or polypeptides may also be used.

In some embodiments, the antigen includes a polynucleotide. The polynucleotide can be DNA or any form of RNA, such as mRNA, miRNA, etc.

EXAMPLES

Synthesis

FIG. 1 shows the synthesis of N-(3-((4-amino-2-butyl-1H-imidazo[4,5-c] quinolin-1-yl)methyl)benzyl)-3,4,5-trihydroxybenzamide (Compound 1).

To a solution of 1.078 grams of 1-(3-(aminomethyl) benzyl)-2-butyl-1H-imidazo[4,5-c]quinolin-4-amine ('IMDQ-m-amine') in pyridine is added 652 mg of 3,4,5-trihydroxybenzoic acid (Gallic acid) and 2.8 g of HATU (1-[bis(dimethylamino)methylene]-1H-1,2,3-triazolo[4,5-b] pyridinium 3-oxide hexafluorophosphate). The mixture is stirred at room temperature for 12 h. The solvent is removed on a rotary evaporator. The solids are dissolved in 5 mL MeOH and subjected to preparative HPLC (C18 column, mobile phase A: water containing 0.1% HCl; mobile phase B: MeOH containing 0.1% HCL). Fractions are checked by analytical LC-MS, and those containing the target Compound 1 are pooled, concentrated, and dried thoroughly. The purity of the final pure solid is verified by LC-MS.

The Compound is chemisorbed onto aluminum hydroxide to form an adjuvant complex referred to herein as ("Alhydroxiquim-II"). The trihydroxybenzyl appendage of the adjuvant Compound 1 ligand-exchanges with the hydroxyl groups of aluminum hydroxide (chemisorption). When appropriate ratios of the adjuvant and aluminum hydroxide are used, all of the adjuvant is bound to alum. This ensures delivery of the adjuvant to the draining lymph nodes, and minimizes systemic exposure. It is important not to exceed the ratio to avoid the presence of excess small molecule adjuvant. The ratio of small molecule adjuvant to aluminum hydroxide gel (Alhydrogel) that has been determined to provide complete binding (and consequent undetectable concentrations of free small molecule) is 10 mg of the small-molecule, N-(3-((4-amino-2-butyl-1H-imidazo[4,5-c] quinolin-1-yl)methyl)benzyl)-3,4,5-trihydroxybenzamide, to 10 mL of standard Alhydrogel (Brenntag, Denmark, 10 mg of aluminum content/mL). The final preparation of aluminum hydroxide chemisorbed with N-(3-((4-amino-2-butyl-1H-imidazo[4,5-c]quinolin-1-yl)methyl)benzyl)-3,4,5-trihydroxybenzamide is referred to as Alhydroxiquim-II.

All references to Alhydroxiquim-II concentrations indicate a nominal aluminum content.

For example, 50 mg of the small molecule chemisorbed on 50 mL (500 mg) of Alhydrogel will yield 500 mg of Alhydroxiquim-II. Accordingly, 50 mg of N-(3-((4-amino-2-butyl-1H-imidazo[4,5-c] quinolin-1-yl)methyl)benzyl)-3,4,5-trihydroxybenzamide is dissolved in a small volume of an appropriate solvent such as 100% ethanol or 100% isopropanol, and added to 50 mL aluminum hydroxide (10 mg/mL, aluminum content) suspension, and stirred for 24 hours. The chemisorption is confirmed by determining that the concentration of N-(3-((4-amino-2-butyl-1H-imidazo[4,5-c] quinolin-1-yl)methyl)benzyl)-3,4,5-trihydroxybenzamide in the supernatant is negligibly low by LC-MS. FIG. 2 shows the chemisorption of N-(3-((4-amino-2-butyl-1H-imidazo[4,5-c] quinolin-1-yl)methyl)benzyl)-3,4,5-trihydroxybenzamide to "Alum" is saturable. Chemisorption was quantified by liquid chromatography-mass spectrometry.

Trafficking of "Alum" nanoparticles chemisorbed with N-(3-((4-amino-2-butyl-1H-imidazo[4,5-c] quinolin-1-yl)methyl)benzyl)-3,4,5-trihydroxybenzamide to draining lymph nodes is shown by FIG. 3. Ten micrograms of material was injected into the footpads of Interferon-beta-Luciferase reporter mice. Interferon-beta-specific luminescence was monitored intravitally.

Figure 4B:
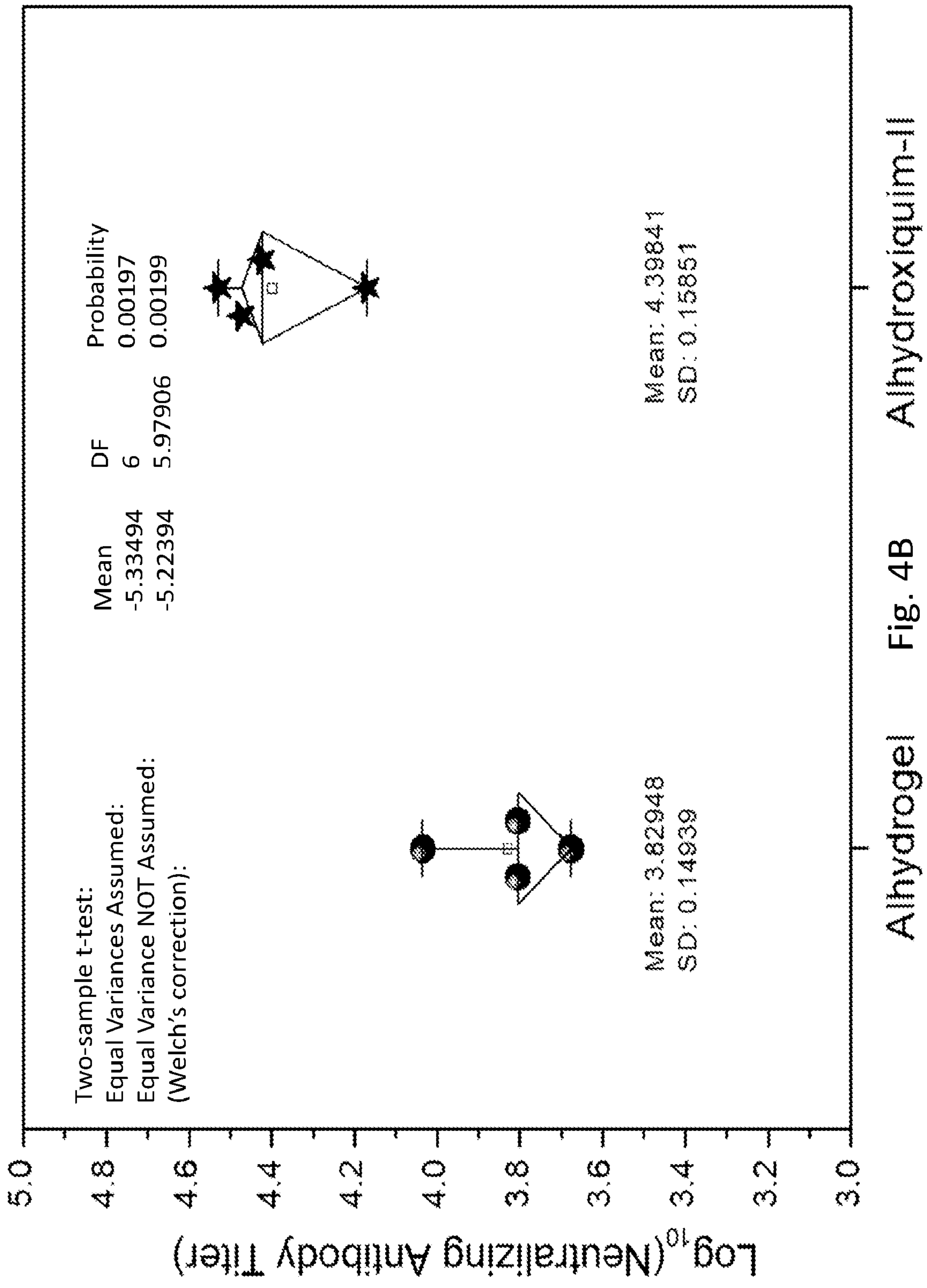
FIG. 4B shows the log 10 of the neutralizing antibody titer for both Alhydrogel and Alhydroxiquim-II.

Induction of neutralizing antibodies to SARS-CoV-2 was performed in rabbits. A comparison of Alhydrogel and Alhydroxiquim-II were performed. As shown in FIGS. 4A-4B, Alhydroxiquim-II elicits higher titers. Rabbits were immunized (prime-boost regimen) with 20 micrograms of SARS-CoV-2 spike protein and 200 micrograms of either Alhydrogel or Alhydroxiquim-II, intramuscularly. The two injections were spaced 14 days apart. FIG. 4A shows the dead cells/mm2 for the serum dilution factors of Alhydrogel and Alhydroxiquim-II. FIG. 4B shows the log 10 of the neutralizing antibody titer for both Alhydrogel and Alhydroxiquim-II.

Figure 5:
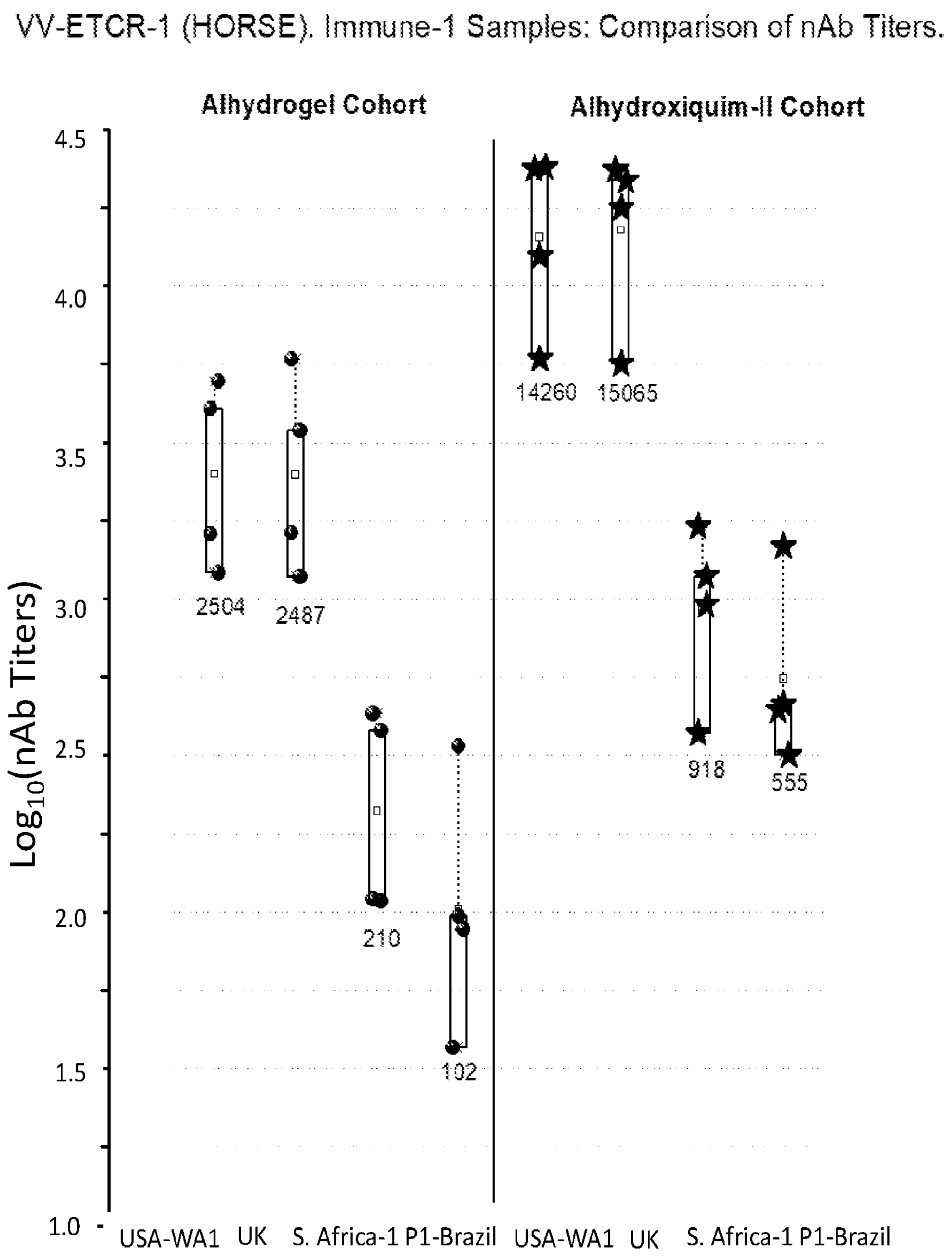
FIG. 5 shows the induction of neutralizing antibodies to SARS-CoV-2 in horses.

Induction of neutralizing antibodies to SARS-CoV-2 was performed in horses. A comparison was performed for Alhydrogel and Alhydroxiquim-II. Horses were immunized (prime-boost regimen) with 20 micrograms of SARS-CoV-2 spike protein and 200 micrograms of either Alhydrogel or Alhydroxiquim-II, intramuscularly. The two injections were spaced 14 days apart. Alhydroxiquim-II elicits higher titers against the wild-type (USA-WA1), UK, South African (S. Africa-1), and Brazilian (P1-Brazil) variants, as shown in FIG. 5. Therefore, it is clear that the Compound 1 in Alhydroxiquim-II functions as an adjuvant for vaccines. It is expected that Compound 1 in Alhydroxiquim-II functions as an adjuvant for vaccines for viruses other than SARS-CoV-2, such as the others recited herein.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

All references recited herein are incorporated herein by specific reference in their entirety:

1. (a) Bergmann-Leitner, E.; Leitner, W., Adjuvants in the Driver's Seat: How Magnitude, Type, Fine Specificity and Longevity of Immune Responses Are Driven by Distinct Classes of Immune Potentiators. *Vaccines* 2014, 2 (2), 252-296; (b) Hunter, R. L., Overview of vaccine adjuvants: present and future. *Vaccine* 2002, 20 Suppl 3, 57-12; (c) Ulmer, J. B.; Valley, U.; Rappuoli, R., Vaccine manufacturing: challenges and solutions. *Nat Biotechnol* 2006, 24 (11), 1377-83.
2. (a) O'Hagan, D. T.; Valiante, N. M., Recent advances in the discovery and delivery of vaccine adjuvants. *Nature reviews. Drug discovery* 2003, 2 (9), 727-35; (b) Mosca, F.; Tritto, E.; Muzzi, A.; Monaci, E.; Bagnoli, F.; Iavarone, C.; O'Hagan, D.; Rappuoli, R.; De Gregorio, E., Molecular and cellular signatures of human vaccine adjuvants. *Proceedings of the National Academy of Sciences of the United States of America* 2008, 105 (30), 10501-6; (c) McKee, A. S.; Munks, M. W.; Marrack, P., How do adjuvants work? Important considerations for new generation adjuvants. *Immunity* 2007, 27 (5), 687-90.
3. Wiley, S. R.; Raman, V. S.; Desbien, A.; Bailor, H. R.; Bhardwaj, R.; Shakri, A. R.; Reed, S. G.; Chitnis, C. E.; Carter, D., Targeting TLRs expands the antibody repertoire in response to a malaria vaccine. *Science translational medicine* 2011, 3 (93), 93ra69.
4. (a) Reed, S. G.; Orr, M. T.; Fox, C. B., Key roles of adjuvants in modern vaccines. *Nature medicine* 2013, 19 (12), 1597-608; (b) Coffman, R. L.; Sher, A.; Seder, R. A., Vaccine adjuvants: putting innate immunity to work. *Immunity* 2010, 33 (4), 492-503.
5 Sansonetti, P. J., The innate signaling of dangers and the dangers of innate signaling. *Nat Immunol* 2006, 7 (12), 1237-42.
6. (a) Akira, S.; Uematsu, S.; Takeuchi, O., Pathogen recognition and innate immunity. Cell 2006, 124 (4), 783-801; (b) Kumagai, Y.; Takeuchi, O.; Akira, S., Pathogen recognition by innate receptors. Journal of infection and chemotherapy: official journal of the Japan Society of Chemotherapy 2008, 14 (2), 86-92; (c) Kawai, T.; Akira, S., The role of pattern-recognition receptors in innate immunity: update on Toll-like receptors. *Nat Immunol* 2010, 11 (5), 373-84.
7. Loo, Y. M.; Gale, M., Jr., Immune signaling by RIG-I-like receptors. *Immunity* 2011, 34 (5), 680-92.
8. (a) Kersse, K.; Bertrand, M. J.; Lamkanfi, M.; Vandenabeele, P., NOD-like receptors and the innate immune system: coping with danger, damage and death. Cytokine & growth factor reviews 2011, 22 (5-6), 257-76; (b) Clarke, T. B.; Weiser, J. N., Intracellular sensors of extracellular bacteria. *Immunol Rev* 2011, 243 (1), 9-25.
9. (a) Hoving, J. C.; Wilson, G. J.; Brown, G. D., Signalling C-type lectin receptors, microbial recognition and immunity. Cellular microbiology 2014, 16 (2), 185-94; (b) Kutikhin, A. G.; Yuzhalin, A. E.; Tsitko, E. A.; Brusina, E. B., Pattern recognition receptors and DNA repair: starting to put a jigsaw puzzle together. Frontiers in immunology 2014, 5, 343; (c) Kawai, T.; Akira, S., The roles of TLRs, RLRs and NLRs in pathogen recognition. *Int Immunol* 2009, 21 (4), 317-37.
10. (a) Krishnan, J.; Lee, G.; Choi, S., Drugs targeting Toll-like receptors. *Arch Pharmacol Res* 2009, 32 (11), 1485-502; (b) Manavalan, B.; Basith, S.; Choi, S., Similar Structures but Different Roles—An Updated Perspective on TLR Structures. *Front Physiol* 2011, 2, 41; (c) Song, D. H.; Lee, J. O., Sensing of microbial molecular patterns by Toll-like receptors. Immunological reviews 2012, 250 (1), 216-29; (d) Kang, J. Y.; Lee, J. O., Structural biology of the Toll-like receptor family. Annu Rev Biochem 2011, 80, 917-41; (e) Takeda, K.; Akira, S., Toll-like receptors. *Curr Protocols Immunol*/edited by John E. Coligan . . . [et al.] 2007, Chapter 14, Unit 14 12; (f) Yu, L.; Wang, L.; Chen, S., Endogenous toll-like receptor ligands and their biological significance. *J Cell Molec Med* 2010, 14 (11), 2592-603.
10. (a) Shizuo Akira, K. T., Tsuneyasu Kaisho, Toll-like receptors—critical proteins linking innate and acquired immunity. Nature Immunology 2001, 2 (8), 675-680; (b) Cottalorda, A.; Verschelde, C.; Marcais, A.; Tomkowiak, M.; Musette, P.; Uematsu, S.; Akira, S.; Marvel, J.; Bonnefoy-Berard, N., TLR2 engagement on CD8 T cells lowers the threshold for optimal antigen-induced T cell activation. European journal of immunology 2006, 36 (7), 1684-93; (c) Kaisho, T.; Akira, S., Toll-like receptors as adjuvant receptors. *Biochim Biophys Acta* 2002, 1589 (1), 1-13.
11. (a) Warshakoon, H. J.; Hood, J. D.; Kimbrell, M. R.; Malladi, S.; Wu, W. Y.; Shukla, N. M.; Agnihotri, G.; Sil, D.; David, S. A., Potential adjuvantic properties of innate immune stimuli. Human vaccines 2009, 5 (6), 381-94; (b) Duthie, M. S.; Windish, H. P.; Fox, C. B.; Reed, S. G., Use of defined TLR ligands as adjuvants within human vaccines. *Immunol Rev* 2011, 239 (1), 178-96; (c) Mastelic, B.; Ahmed, S.; Egan, W. M.; Del Giudice, G.; Golding, H.; Gust, I.; Neels, P.; Reed, S. G.; Sheets, R. L.; Siegrist, C. A.; Lambert, P. H., Mode of action of adjuvants: implications for vaccine safety and design. Biologicals:

Journal of the International Association of Biological Standardization 2010, 38 (5), 594-601.

12. (a) Pockros, P. J., Guyader, D., Patton, H., Tong, M. J., Wright, T., McHutchison, J. G., and Meng, T. C. (2007) Oral resiquimod in chronic HCV infection: Safety and efficacy in 2 placebo-controlled, double-blind phase IIa studies. *J. Hepatol.* 47, 174-182. (b) Sauder, D. N., Smith, M. H., Senta-McMillian, T., Soria, I., and Meng, T. C. (2003) Randomized, single-blind, placebo-controlled study of topical application of the immune response modulator resiquimod in healthy adults. *Antimicrob. Agents Chemother.* 47, 3846-3852. (c) Szeimies, R. M., Bichel, J., Ortonne, J. P., Stockfleth, E., Lee, J., and Meng, T. C. (2008) A phase II dose-ranging study of topical resiquimod to treat actinic keratosis. Br. J. Dermatol. 159, 205-210.

13. (55) Wu, T. Y., Singh, M., Miller, A. T., De Gregorio, E., Doro, F., D'Oro, U., Skibinski, D. A., Mbow, M. L., Bufali, S., Herman, A. E., et al. (2014) Rational design of small molecules as vaccine adjuvants. *Sci. Transl. Med.* 6, 263ra160.

14. David, S. A. Presentation at the Adjuvant Meeting, NIAID, Bethesda, MD, November 2019.

The invention claimed is:

1. A compound of the structure of Compound 1,

Compound 1

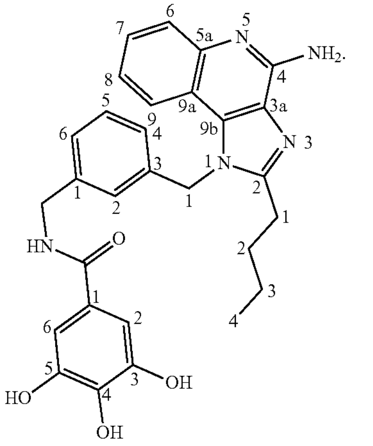

2. A composition comprising:

the compound of claim 1;

an aluminum hydroxide particle; and a pharmaceutical carrier having the compound.

3. The composition of claim 2, further comprising at least one immunogen or antigen.

4. The composition of claim 3, wherein the antigen is chemically modified with formaldehyde, glutaraldehyde, beta-propiolactone, or combinations thereof.

5. The composition of claim 3, wherein the antigen includes an inactivated viral, bacterial, or fungal pathogen.

6. The composition of claim 3, wherein the antigen includes a polypeptide, protein, or portion thereof.

7. The composition of claim 3, wherein the antigen includes at least part of an allergen, a polypeptide, a toxin, a chemically inactivated toxin (toxoid), an inactivated virus, an inactivated bacterium, or an inactivated fungus that includes the antigen.

8. A complex comprising:

the compound of claim 1; and an aluminum hydroxide particle having the compound associated therewith.

9. The complex of claim 8, wherein the association of Compound 1 with the aluminum hydroxide particle occurs via chemisorption.

10. A method of performing a vaccination, the method comprising:

providing the composition of claim 3; and administering the composition to a subject to provide a complex of the compound and the aluminum hydroxide in an amount sufficient to function as an adjuvant.

11. A method of agonizing a TLR 7 and/or TLR 8, the method comprising:

providing the compound of claim 1 to TLR 7 and/or TLR 8 in an amount sufficient to agonize the TLR 7 and/or TLR 8; and agonizing the TLR7 and/or TLR8 so as to cause an adaptive immune response to an antigen.

12. A method of synthesizing the Compound 1 of claim 1, the method comprising:

reacting 1-(3-(aminomethyl)benzyl)-2-butyl-1H-imidazo[4,5-c]quinolin-4-amine with 3,4,5-trihydroxybenzoic acid (gallic acid), along with a coupling agent, to form the Compound 1.

* * * * *